(12) United States Patent
Santilli

(10) Patent No.: US 6,572,619 B2
(45) Date of Patent: Jun. 3, 2003

(54) CAGE PLATE FOR SPINAL FUSION AND METHOD OF OPERATION

(76) Inventor: Albert N. Santilli, 28326 Gates Mill Blvd., Pepper Pike, OH (US) 44124

( * ) Notice: Subject to any disclaimer, the term of this patent is extended or adjusted under 35 U.S.C. 154(b) by 70 days.

(21) Appl. No.: 09/792,694

(22) Filed: Feb. 23, 2001

(65) Prior Publication Data

US 2002/0151893 A1 Oct. 17, 2002

(51) Int. Cl.$^7$ ................................................ A61B 17/56
(52) U.S. Cl. ........................ 606/61; 606/69; 623/17.16
(58) Field of Search .............................. 606/61, 70, 71, 606/72, 60, 69; 623/17.16, 17.11, 11.11

(56) References Cited

U.S. PATENT DOCUMENTS

| | | | |
|---|---|---|---|
| 4,892,545 A | * | 1/1990 | Day et al. ...................... 606/61 |
| 5,382,248 A | | 1/1995 | Jacobson et al. |
| 5,611,800 A | | 3/1997 | Davis et al. |
| 5,749,875 A | * | 5/1998 | Puddu .......................... 606/69 |
| 5,961,554 A | * | 10/1999 | Janson et al. .................. 606/61 |
| 6,066,175 A | * | 5/2000 | Henderson et al. ......... 623/17.11 |
| 6,231,610 B1 | * | 5/2001 | Geisler ..................... 623/17.11 |
| 6,235,059 B1 | * | 5/2001 | Benezech et al. ............. 606/61 |
| 6,395,030 B1 | * | 5/2002 | Songer et al. ........... 623/17.11 |

* cited by examiner

*Primary Examiner*—Pedro Philogene
(74) *Attorney, Agent, or Firm*—Rankin, Hill, Porter & Clark LLP

(57) ABSTRACT

A cage plate for spinal fusion includes a cage made of a biologically inert material such as titanium, the cage being sufficiently porous to facilitate bony ingrowth and spinal fusion, and a plate to which the cage is attached, the plate being made of a biologically inert material such as titanium. In the preferred embodiment, the plate is generally rectangular and has a longitudinal axis that in use is disposed parallel with the longitudinal axis of the spinal column, the plate being curved when viewed from the end, the curvature approximating that of the vertebral bodies to be fused, and the plate being curved when viewed from the side, the curvature approximating that of the vertebral bodies to be fused. The plate includes a plurality of openings adjacent its corners. In use, an opening is formed in the spinal column of approximately the same size and shape as the cage. The cage is inserted into the opening. In addition, several small openings are formed in the vertebral bodies. Bone screws are inserted through the openings in the plate and into the small openings in the vertebral bodies. The plate and the cage thus are secured to the vertebral bodies and the vertebral bodies are immobilized.

8 Claims, 3 Drawing Sheets

FIG. 5

1. Use customary and general techniques to achieve maximum surgical exposure to the anterior cervical anterior vertebral body.

2. Determine which size implant to use (via x-ray templates), then use the same size "jig template" to mark proximal and distal location cage plate. Use a #1 Midis Rex or Anspach to score proximal and distal and side slots. A "step drill burr" is required.

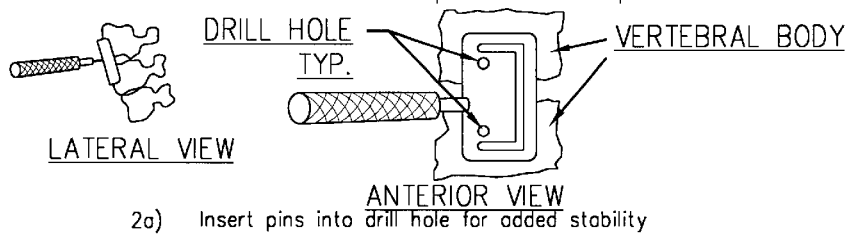

2a) Insert pins into drill hole for added stability

3. Turn jig template upside down to cut entire circumference.

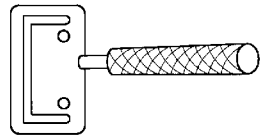

4. Finish removing and cleaning the rectangular block of bone to assure good press fit of cervical cage plate – use an end mill with depth gage and end-mill jig.

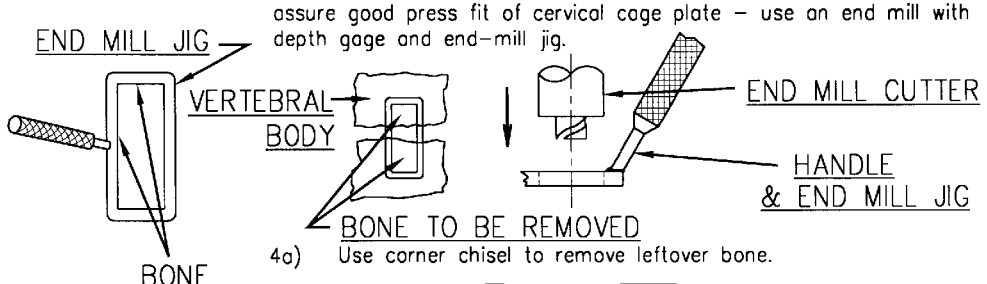

4a) Use corner chisel to remove leftover bone.

5. Insert cage plate. Drill hole for screws using a depth gage. Screw in plate.

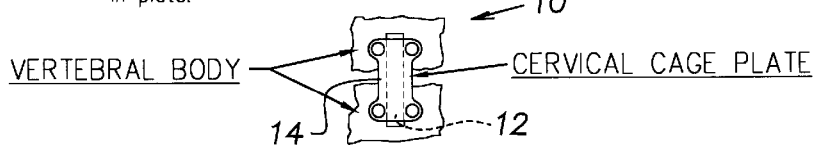

CAGE PLATE FOR SPINAL FUSION AND METHOD OF OPERATION

REFERENCE TO RELATED PATENT AND RELATED PROVISIONAL APPLICATION

Reference is made to U.S. Pat. No. 5,961,554, issued Oct. 5, 1999 to Frank S. Janson and Albert N. Santilli, the disclosure of which is incorporated herein by reference. Reference also is made to provisional application serial No. 60/117,487, filed Jan. 25, 2000 by Albert N. Santilli, the disclosure of which is incorporated herein by reference and from which priority is claimed.

BACKGROUND OF THE INVENTION

1. Field of the Invention

The invention relates to spinal fusion and, more particularly, to the fusion of vertebral bodies through the use of a cage plate.

2. Description of the Prior Art

Techniques and devices for fusing two or more vertebrae of the spine together are well known. Such techniques are commonly performed to correct problems, such as chronic back pain, which result from degenerated intervertebral discs. One technique for fusing together two or more vertebrae of the lumbar spine includes excising a portion of the disc extending between adjacent vertebrae and grafting one or more portions of bone of a desired shape, known as an intervertebral spacer, between the adjacent vertebrae. The intervertebral spacer may be inserted by either an anterior or posterior approach to the spinal column depending on a number of factors, including the number of vertebrae to be fused and past operative procedures. Upon healing, the vertebrae are desirably fused together through the intervertebral spacer.

Conventionally, intervertebral spacers have been autogenic bone harvested from other areas of the body, such as the pelvis, allogenic bone taken from cadavers or xenogenic bone, such as bovine bone sections. However, the use of bone grafts can add complications to the fusion procedure. For example, when using an autogenic bone graft, a second incision must be made in the patient to harvest the additional bone to be used in the graft, thus increasing the pain and blood loss to the patient. When allogenic or xenogenic bone grafts are used there is a potential for the transmission of disease or infection from the cadaver or other graft source to the patient, as well as rejection of the graft.

The use of non-biological implants, such as carbon fiber spacers, also has been attempted in the past, but these spacers tend to lack sufficient porosity and tissue ingrowth characteristics to function adequately. However, the spacer disclosed in U.S. Pat. No. 5,961,554 is made of sintered titanium beads which provide excellent porosity and strength.

Apart from spacers per se, spinal fusion has been accomplished by attaching various external devices such as rods that are screwed to adjacent vertebral bodies. Examples of such devices are disclosed in U.S. Pat. Nos. 5,382,248 and 5,611,800. These types of devices are versatile in the sense that both adjacent vertebrae and spaced vertebrae can be fused, depending on the patient's needs. Unfortunately, although such devices have been used successfully, they are complex to manufacture and are difficult to install, thereby prolonging the surgical installation procedure. Furthermore, they do not have the capability to provide bony ingrowth that will occur when porous spacers are used.

It would be desirable to have a non-biological spacer which is non-reactive in the body and which has the strength and tissue ingrowth characteristics of a bone graft spacer. It also would be desirable to have a spinal fusion technique that has the strength and versatility of known rod and screw techniques without the installation difficulties associated therewith.

SUMMARY OF THE INVENTION

In response to the foregoing concerns, the present invention provides a porous intervertebral spacer, or cage, that can be used in the same manner as a bone graft spacer to fuse vertebrae together. The present invention also includes a plate to which the cage is attached. The plate is connected to the vertebral bodies that are being fused together, preferably by the use of bone screws. In combination, the cage and the plate provide superior fusion capability and strength, ease of installation, and bony ingrowth characteristics.

The cage according to the invention can be made of a variety of substances that are inert to the body and which will not be rejected by the body. Sintered titanium or titanium alloy beads or wire mesh of titanium or titanium alloys as disclosed in U.S. Pat. No. 5,961,554 are the preferred materials for the cage. Another possibility is pellets of PEEK (polyaryl, ether, ether ketone) polymer or other strong polymers sintered in a mold of a desired shape and size. Other suitable materials include cobalt-chromium alloys, tantalum, tantalum alloys, niobium, niobium alloys, and stainless steel. Provided an appropriate material is chosen, the cage will be non-biologically reactive and will provide for tissue ingrowth to facilitate fusion with adjacent vertebrae. A solid metal or polymer cage also can be made porous by machining or otherwise forming holes or cavities throughout the cage. The cage can be formed in a variety of shapes such as a prism (for example, a rectangular prism), a cylinder, or a plate. Generally, it is expected that the cage will be a vertically oriented strut having a square or rectangular cross-section.

The plate to which the cage is attached preferably is a thin, generally rectangular member that is made of the same material as the cage. The plate includes openings at or near its corners through which bone screws can extend. In top view the plate is curved, with a radius of approximately 40 mm. In side elevation, the plate either can be straight or curved, with a radius of approximately 100 mm when curved. The amount of curvature, if any, is a function of the particular vertebrae to which the plate is to be connected. The plate can be formed in other shapes, if desired.

The foregoing and other features and advantages of the invention are described in more detail in the accompanying specification, claims, and drawings.

BRIEF DESCRIPTION OF THE DRAWINGS

FIG. 5 is an illustration showing and describing the sequential steps by which the cage plate according to the invention is installed in a patient.

DESCRIPTION OF THE PREFERRED EMBODIMENT

Figure 1A:
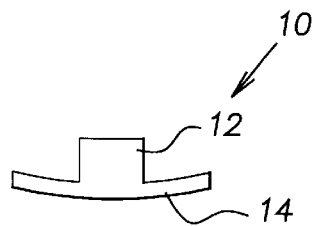
FIGS. 1A, 1B, and 1C are top, front, and side elevation views of a cage plate in accordance with the invention, the plate being shown in a straight configuration.
Figure 1B:
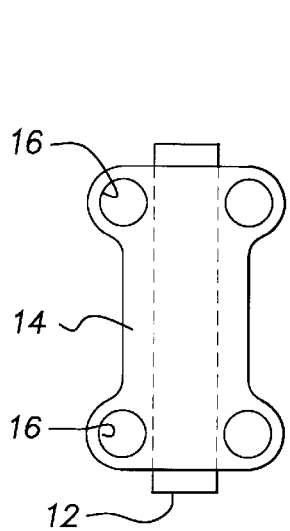
Figure 1C:
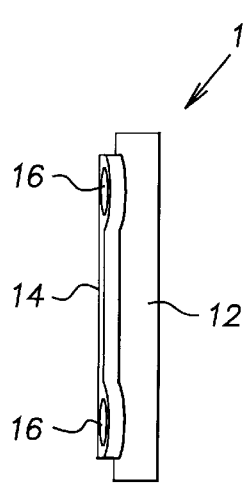
Figure 1D:
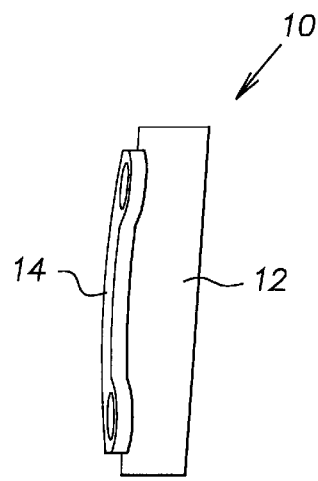
FIG. 1D is a view similar to FIG. 1C in which the plate is curved.

With reference to the drawings and initially to FIGS. 1A–1F, a cage plate according to the invention is indicated by the reference numeral 10. The cage plate 10 includes a spacer portion, or cage 12, in the form of a porous biologically inert block in the form of a rectangular prism. The corners of the cage 12 may be formed with a small radius if desired. The cage 12 is sized to fit within an opening or graft bed formed between adjacent vertebrae by the surgical excision of a portion of the intervertebral disc and confronting portions of the adjacent vertebral bodies. The particular size of the cage 12 will be determined by the particular vertebrae to be fused, and condition of the vertebrae. Advantageously, because the cage 12 is not made of a biological material, it can be easily stored and can be manufactured in a variety of shapes and sizes to accommodate anticipated situations. A typical cage 12 for fusing vertebrae of the lumbar spine may be from 10 to 13 millimeters in width, 8 to 24 millimeters in height, and 25 to 30 millimeters in length. The table shown below illustrates the various dimensions of typically sized cages 12.

| MODEL | HEIGHT (H) | WIDTH (W) | LENGTH (L) |
| --- | --- | --- | --- |
| STRAIGHT | | | |
| 1 | 25 mm | 5 mm | 6 mm |
| 2 | 32 mm | 5 mm | 6 mm |
| 3 | 40 mm | 5 mm, 7 mm | 6 mm, 8 mm |
| 4 | 47 mm | 5 mm, 7 mm | 6 mm, 8 mm |
| 5 | 58 mm | 6 mm, 8 mm | 10 mm |
| CURVED | | | |
| 1C | 25 mm | 5 mm | 6 mm |
| 2C | 32 mm | 5 mm | 6 mm |
| 3C | 40 mm | 5 mm, 7 mm | 6 mm, 8 mm |
| 4C | 47 mm | 5 mm, 7 mm | 6 mm, 8 mm |
| 5C | 58 mm | 6 mm, 8 mm | 10 mm |

It will be appreciated that while a specific example of the intervertebral cage 12 described herein is with reference to a cage for fusing vertebrae of the cervical spine, the invention applies also to cages 12 for fusing vertebrae of the lumbar or thoracic spine as well. The particular shape of the cage 12 also is a function of the application. While a generally rectangular cage 12 is well suited to fusing cervical or lumbar vertebrae, in other instances other shapes for the cage 12, such as cylindrical or wedge-shaped, may be desirable. Moreover, it will be recognized that the cages 12 of the invention may also be used in other areas of the body to fuse bone together where necessary.

The cage 12 preferably is made of biologically inert beads or pellets having a diameter such as to yield, when fused, a cage 12 with the fused beads or pellets occupying a range of generally 45 to 75 percent of the volume of the cage 12 (voids thereby constituting 25–55% of the volume of the cage 12). For convenience of description, all small solid particles such as beads, pellets, grains, and the like that are suitable for use with the invention will be referred to hereafter as "beads." This porosity described herein provides a cage 12 which is sufficiently porous throughout to allow for the flow of bodily fluids through the cage 12 and to promote tissue ingrowth and bony fusion with adjacent vertebrae. The beads also result in textured, porous surfaces over the cage 12 which when implanted develop a high-friction interface with the vertebral bodies to facilitate maintaining the cage 12 in place.

The beads preferably are composed of titanium, titanium alloy, or high strength polymers. A particularly desirable polymer is PEEK (polyaryl, ether, ether ketone) resin which is believed to be non-reactive within the body, or other high strength materials that are inert in the body. PEEK polymer is a high performance thermoplastic polymer made by Victrex plc of Westchester, Pa. PEEK polymer is semi-crystalline and is insoluble in all common solvents and has excellent resistance to a wide range of organic and inorganic liquids. The polymer retains excellent mechanical properties up to 572° F. It also can resist high dose levels of gamma radiation. It is an excellent choice for spinal implants and similar applications because it has a low value of coefficient of linear thermal expansion ($2.6 \times 10^{-5}$° F. by ASTM D696) up to the high glass transition temperature of 289° F. ($T_g$ by DSC).

It has been found that beads of a certain size range are preferred. Suitable small beads will have a mesh size of −45 +60 (0.009 inch to 0.011 inch). Suitable medium beads will have a mesh size of −25 +30 (0.016 inch to 0.027 inch). Suitable large beads will have a mesh size of −18 +30 (0.032 inch to 0.046 inch). The size of the beads determines the porosity of the finished cage 12. The larger the beads, the greater the porosity. In certain applications, it may be desirable to mix beads of various sizes to obtain a finished cage 12 having a variable porosity.

It is possible to intermix fibers of PEEK polymer with the PEEK beads to form a cage 12 having variable qualities of strength and porosity. Similarly, titanium fibers can be intermixed with titanium beads. In general, the use of fibers results in a stronger, less porous cage 12. It also is possible to form the cage 12 entirely of fibers. A solid metal or polymer cage 12 also can be made porous by machining or otherwise forming holes or cavities throughout the cage 12. Other materials suitable for use in making the cage 12 include one or more of the following materials: cobalt-chromium alloys, tantalum, tantalum alloys, niobium, niobium alloys, and stainless steel.

One method of fusing metal or polymer beads to form the cage 12 includes placing the beads into a cavity within a mold. The mold preferably is a three-piece mold forming a cavity of the finished dimensions of the cage 12. The mold containing the beads then is heated to a temperature high enough to cause sintering to occur. Other methods for fusing beads or fibers which provide a sufficiently strong cage 12 also may be acceptable. When fibers are used to form the cage 12, the fibers are placed in the mold in a tangled, tortuous mass. Sintering produces strong inter-strand bonds with variably sized openings to form a cage 12 of suitable strength and porosity.

In FIG. 1, the cage 12 is attached to a plate 14 made of a biologically inert material such as stainless steel or titanium. It also is possible to form the plate from a high strength polymer such as PEEK or metals such as cobalt-chromium alloys, tantalum, tantalum alloys, niobium, niobium alloys, and stainless steel. Preferably, the cage 12 and the plate 14 will be made of the same material. Typically, the cage 12 and the plate 14 will be fused to each other during the sintering process that produces the cage 12. If the cage 12 and the plate 14 are made of metal, the cage 12 can be welded to the plate 14. The particular type of attachment process is not important so long as (1) it utilizes materials that are inert in the body and (2) the cage 12 and the plate 14 cannot be separated from each other after installation in a patient.

The plate 14 has an opening 16 at each corner through which a screw or other fastener can be inserted. It is expected that the cage 12 will be installed vertically in a patient's spine (with the longitudinal axis of the cage 12 oriented vertically as shown in the drawings). When viewed from the end, the plate 14 is curved, with a radius of 40 mm. When viewed from the side, the plate 14 can be straight or curved. If curved, the plate 14 has a radius of approximately 100 mm. Due to the curvature of the plate 14 about its longitudinal axis, the screws inserted through the openings 16 will be inclined toward the longitudinal axis at an angle of about 15 degrees.

Figure 1E:
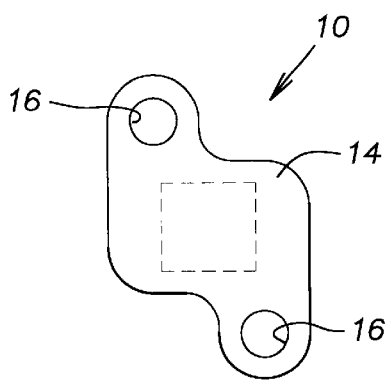
FIGS. 1E and 1F are front and side elevations views of an alternate form of cage plate according to the invention.
Figure 1F:
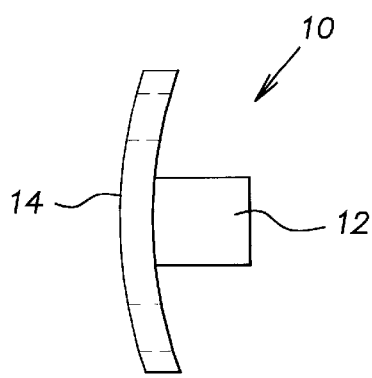

As indicated previously, various sizes of the cage 12 are shown in the table set forth above. It is to be understood that the dimensions of the cage 12 can be chosen to suit the needs of the patient. In particular, although the cage 12 is illustrated in FIGS. 1A–1D as having a larger vertical dimension than the plate 14, it is expected that the cage 12 frequently will have a smaller vertical dimension than the plate 14. Indeed, it is entirely possible and desirable that the cage 12 will have a smaller vertical dimension than the distance between the openings 16 on opposite ends of the plate 14. FIGS. 1E and 1F illustrate such an arrangement, as well as the use of a non-rectangular plate 14.

The procedure for fusing two or more vertebrae together using the cage plate 10 of the invention is substantially the same as the procedure for fusing vertebrae using a bone graft, but without many of the complications due to obtaining a suitable bone graft and the possibility of transmitting disease from the bone graft donor. One anterior procedure for implanting a bone graft to fuse vertebra of the lumbar spine is discussed in Collis et al., "*Anterior Total Disc Replacement: A Modified Anterior Lumbar Interbody Fusion,*" Lumbar Interbody Fusion, ed. Robert Watkins, Chapter 13, pp. 149–152, Aspen Publications (1989), the disclosure of which is incorporated herein by reference.

Figure 2:
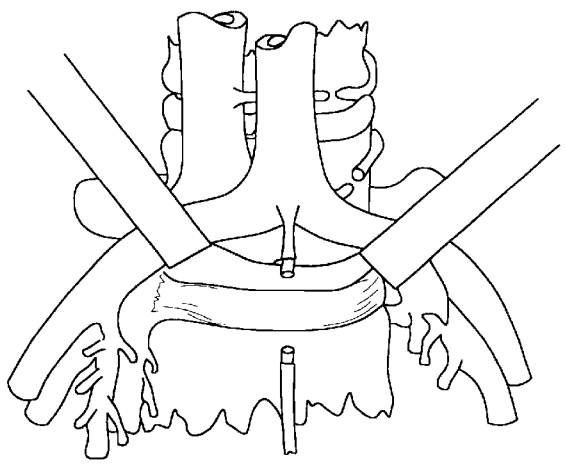
FIG. 2 is an elevation view of the anterior of a portion of the cervical spine.
Figure 3:
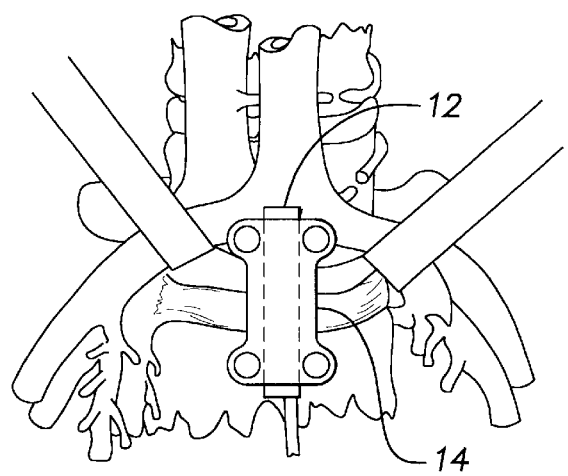
FIG. 3 is a view similar to FIG. 2 in which a cage plate according to the invention has been installed.
Figure 4:
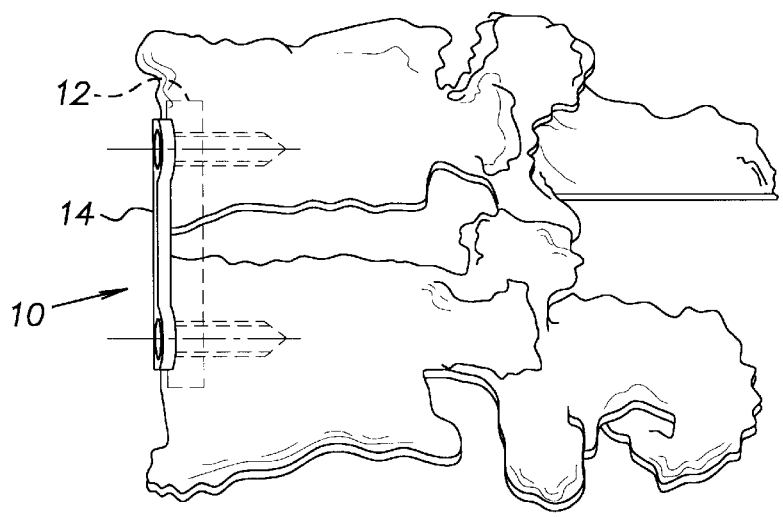
FIG. 4 is a side elevation view of two representative vertebrae in which a cage plate according to the invention has been installed.

Referring to FIGS. 2–4, anterior views and a side elevation view of the cervical spine are shown. The cage 12 of the cage plate 10 is installed in the same manner as is described in U.S. 5,961,554 at columns 4–5. The description set forth in FIG. 5 describes a step-by-step methodology for installing the complete cage plate 10 in adjacent cervical vertebral bodies. It is to be understood that the length of the plate 14 and the cage 12 can be selected to fuse either two or three vertebrae of any portion of the spine.

It is to be understood that the present disclosure of the preferred embodiment has been made only by way of example, and that various changes may be resorted to without departing from the true spirit and scope of the invention as hereinafter claimed. It is intended that the patent shall cover, by suitable expression in the appended claims, whatever degree of patentable novelty exists in the invention disclosed.

What is claimed is:

1. A cage plate for fusing selected vertebral bodies of a patient's spinal column in which an opening has been formed, comprising:
   a cage made of a biologically inert material, the cage having voids that constitute approximately 25 to 55 percent of the volume of the cage and being sufficiently porous to facilitate bony ingrowth and spinal fusion, the cage adapted to be inserted into the opening in the spinal column; and
   a plate to which the cage is attached, the plate being made of a biologically inert material, the plate adapted to be connected to the spinal column.

2. The cage plate of claim 1, wherein the cage is made of one or more materials selected from the group consisting of titanium, titanium alloys, PEEK (polyaryl, ether, ether ketone) polymer, cobalt-chromium alloys, tantalum, tantalum alloys, niobium, niobium alloys, and stainless steel.

3. The cage plate of claim 1, wherein the plate is generally rectangular and has a longitudinal axis that in use is disposed parallel with the longitudinal axis of the spinal column, the plate being curved when viewed from the top, the curvature approximating that of the vertebral bodies to be fused, and the plate being curved when viewed from the side, the curvature approximating that of the vertebral bodies to be fused.

4. The cage plate of claim 1, further comprising means for attaching the plate to the vertebral bodies.

5. The cage plate of claim 4, wherein the means for attaching the plate to the vertebral bodies includes a plurality of openings in the plate and bone screws that can be screwed into the vertebral bodies through the openings in the plate.

6. A cage plate for fusing selected vertebral bodies of a patient's spinal column in which an opening has been formed; comprising:
   a cage made of one or more biologically inert materials selected from the group consisting of titanium, titanium alloys, PEEK (polyaryl, ether, ether ketone) polymer, cobalt-chromium alloys, tantalum, tantalum alloys, niobium, niobium alloys, and stainless steel, the cage having voids that form a porosity within the range of about 25 to 55 percent of the volume of the cage and being able to facilitate bony ingrowth and spinal fusion, the cage adapted to be inserted into the opening in the spinal column; and
   a plate to which the cage is attached, the plate being made of a biologically inert material selected from the group consisting of titanium, titanium alloys, PEEK (polyaryl, ether, ether ketone) polymer, cobalt-chromium alloys, tantalum, tantalum alloys, niobium, niobium alloys, and stainless steel, the plate adapted to be connected to the spinal column, the plate being generally rectangular and having a longitudinal axis that in use is disposed parallel with the longitudinal axis of the spinal column, the plate being curved when viewed from the top, the curvature approximating that of the vertebral bodies to be fused, and the plate being curved when viewed from the side, the curvature approximating that of the vertebral bodies to be fused, the plate having a plurality of openings adjacent the corners thereof through which bone screws can be inserted and screwed into the vertebral bodies.

7. A method for fusing vertebral bodies of a patient's spinal column, comprising the steps of:
   providing a cage made of a biologically inert material, the cage having voids that constitute approximately 25 to 55 percent of the volume of the cage and being sufficiently porous to facilitate bony ingrowth and spinal fusion;
   providing a plate, the plate being made of a biologically inert material;
   attaching the cage to the plate;
   forming an opening in the spinal column;
   inserting the cage in the opening; and
   connecting the plate to the vertebral bodies to be fused.

8. The method of claim 7, wherein the step of connecting is accomplished by:
   forming openings in the plate;
   forming openings in the vertebral bodies to be fused;
   providing bone screws; and
   inserting the bone screws into the vertebral bodies through the openings in the plate.

* * * * *